US010736902B2

(12) United States Patent
Redmond et al.

(10) Patent No.: US 10,736,902 B2
(45) Date of Patent: Aug. 11, 2020

(54) METHOD OF TREATING TRIPLE NEGATIVE BREAST CANCER

(71) Applicant: GEISTLICH PHARMA AG, Wolhusen (CH)

(72) Inventors: H. Paul Redmond, Wilton Cork (IE); Rolf W. Pfirrmann, Weggis (CH)

(73) Assignee: GEISTLICH PHARMA AG, Wolhusen (CH)

( * ) Notice: Subject to any disclaimer, the term of this patent is extended or adjusted under 35 U.S.C. 154(b) by 0 days.

(21) Appl. No.: 16/085,294

(22) PCT Filed: Mar. 17, 2017

(86) PCT No.: PCT/IB2017/051570
§ 371 (c)(1),
(2) Date: Sep. 14, 2018

(87) PCT Pub. No.: WO2017/158570
PCT Pub. Date: Sep. 21, 2017

(65) Prior Publication Data
US 2019/0091233 A1 Mar. 28, 2019

Related U.S. Application Data

(60) Provisional application No. 62/310,275, filed on Mar. 18, 2016.

(51) Int. Cl.
| *A61K 31/54* | (2006.01) |
| *A61K 38/20* | (2006.01) |
| *A61K 45/06* | (2006.01) |
| *A61K 31/549* | (2006.01) |
| *A61K 31/541* | (2006.01) |
| *A61P 35/00* | (2006.01) |

(52) U.S. Cl.
CPC ........... *A61K 31/54* (2013.01); *A61K 31/541* (2013.01); *A61K 31/549* (2013.01); *A61K 38/2013* (2013.01); *A61K 45/06* (2013.01); *A61P 35/00* (2018.01)

(58) Field of Classification Search
CPC ........ A61K 38/20; A61K 45/00; A61K 31/54; A61K 31/541; A61P 35/00
USPC ................ 514/222.5, 435; 544/2, 8; 549/18
See application file for complete search history.

(56) References Cited

FOREIGN PATENT DOCUMENTS

| EP | 1201247 A2 | 5/2002 |
| EP | 1304111 A2 | 4/2003 |
| WO | 2013/190355 A1 | 12/2013 |

OTHER PUBLICATIONS

Maluta et al., Role of Hyperthermia in Breast Cancer Locoregional Recurrence: A Review, Breast Care, 10:408-412 (2015).*
Hanan Ahmed Wahba et al., "Current approaches in treatment of triple-negative breast cancer", Cancer Biol Med, vol. 12, Jan. 1, 2015 (Jan. 1, 2015), pp. 106-116.
Simon Zeichner et al., "A Review of Systemic Treatment in Metastatic Triple-Negative Breast Cancer", Breast Cancer: Basic and Clinical Research, vol. 10, Feb. 9, 2016 (Feb. 9, 2016), pp. 25-36.
Meena S Moran "Radiation therapy in the locoregional treatment of triple-negative breast cancer", The Lancet. Oncology, Mar. 1, 2015 (Mar. 1, 2015), pp. e113-e122.
International Preliminary Report on Patentability cited in PCT/IB2017/051570 dated Sep. 18, 2018, 8 pages.
"FDA approves atezolizumab for PD-L1 positive unresectable locally advanced or metastatic triple-negative breast cancer," U.S. Food & Drug Administration press release dated Mar. 8, 2019, available at https://www.fda.gov/drugs/drug-approvals-and-databases/fda-approves-atezolizumab-pd-l1-positive-unresectable-locally-advanced-or-metastatic-triple-negative, 2 pages.
"Guidance for Industry Expedited Programs for Serious Conditions—Drugs and Biologics," U.S. Food & Drug Administration, May 2014, available at https://www.fda.gov/files/drugs/published/Expedited-Programs-for-Serious-Conditions-Drugs-and-Biologics.pdf, 40 pages.
Decision in *OSI Pharm., LLC* v. *Apotex Inc.*, 939 F.3d 1375, 1377 (Fed. Cir. 2019), dated Oct. 4, 2019, 11 pages.

* cited by examiner

*Primary Examiner* — Deepak R Rao
(74) *Attorney, Agent, or Firm* — Rothwell, Figg, Ernst & Manbeck, P.C.

(57) ABSTRACT

A method of treating a patient suffering from TNBC by a multidisciplinary method involving treating the patient with a plurality of the following treatments: i) one or more checkpoint inhibitors; ii) hyperthermia treatment; iii) low dose chemotherapy; iv) Interleukin-2 (IL-2); and v) a compound selected from the group consisting of taurolidine, taurultam, oxathiazin-like compounds, and combinations thereof.

21 Claims, 8 Drawing Sheets

METHOD OF TREATING TRIPLE NEGATIVE BREAST CANCER

CROSS REFERENCE TO RELATED APPLICATION

This application is a 35 U.S.C. 371 National Phase Entry Application from PCT/162017/051570, filed Mar. 17, 2017, which claims the benefit of U.S. Ser. No. 62/310,275 filed on Mar. 18, 2016, the disclosure of which is incorporated herein in its entirety by reference.

BACKGROUND OF THE INVENTION

Field of the Invention

The present invention relates to a method for treating a patient diagnosed with triple negative breast cancer.

Description of the Background Art

Breast cancer is the most common form of cancer in women. Breast cancer is a heterogeneous disease having diverse physiological characteristics and clinical responses. Breast cancer types are divided based on receptor expression.

There are three molecules that have been identified to promote many breast cancers: estrogen receptor (ER), progesterone receptor (PR), and human epidermal growth factor receptor 2 (HER2).

Triple-negative breast cancer ("TNBC") refers to any breast cancer that does not express the genes for estrogen receptor (ER), progesterone receptor (PR) or Her2/neu (HER2) and represents about 15% of breast cancers. Tumors that express ER and PR are treated with agents that interfere with hormone production or action. Tumors that have amplified HER-2/Neu are treated with agents that inhibit HER-2/Neu. This makes TNBC more difficult to treat because most chemotherapies target one of the three receptors. Triple-negative breast cancers have a relapse pattern that is very different from hormone-positive breast cancers: the risk of relapse is much higher for the first 3-5 years, but drops sharply and substantially below that of hormone-positive breast cancers after that. TNBC is thus very aggressive and has the worst prognosis of breast cancer types. This relapse pattern has been recognized for all types of triple-negative cancers for which sufficient data exists although the absolute relapse and survival rates differ across subtypes. TNBC is typically high grade (poorly differentiated) and rapidly progressive, with a higher risk of relapse and lower survival than other subtypes of breast cancer.

Conventional treatments are limited by poor therapeutic response, high toxicity, and the development of resistance. The lack of clinically significant outcomes from conventional systemic as well as combination therapies, e.g., involving chemotherapy, radiation and immune therapy, despite their ability to prime and expand tumor antigen-specific T cells may at least partly be attributed to the inability of therapy-induced T-cell responses to overcome the tumoral mechanisms of immune escape that limit the clonal expansion of T cells following such triple therapy. A number of such mechanisms have been recognized including increased tumoral pressure, reduced antigen presentation, antigenic loss, cytokines, immunosuppressive cells and immune checkpoints.

In view of these problems, an object of the present disclosure is to provide a safe, tolerable and effective method for treating patient suffering from TNBC. These and other objects have been achieved according to the present disclosure.

SUMMARY OF THE INVENTION

In accordance with the present disclosure, methods and compositions for treating a patient suffering from TNBC are disclosed. According to the present disclosure, taurolidine and C-2250 can be used as neoadjuvant treatments perioperatively for treatment of breast cancer, including primary as well as metastatic. These compounds can be used alone and in combination with other (co) treatment especially hormone and are especially advantageous for long term use in TNBC post-operatively, e.g., for at least 5-10 years. C-2250 has been identified as being particularly useful as an oral therapy for patients diagnosed with TNBC. C-2250 is effective against multiple TNBC cell lines, has a long half-life in humans, and is tolerable and safe.

One aspect of the present disclosure is a method of treating a patient suffering from triple negative breast cancer (TNBC) comprising treating the patient with taurolidine, taurultam, one or more oxathiazin-like compounds, or a combination thereof, or treating the patient with a plurality of treatments selected from the group consisting of one or more checkpoint inhibitors, hyperthermia, low dose chemotherapy, and Interleukin-2 (IL-2) co-therapy with a compound selected from the group consisting of taurolidine, taurultam, one or more oxathiazin-like compounds, and combinations thereof.

In one aspect, the patient is treated with taurolidine, taurultam, one or more oxathiazin-like compounds, or a combination thereof administered intravenously, orally or a combination thereof.

In one aspect, the patient is treated with taurolidine, taurultam, one or more oxathiazin-like compounds, or a combination thereof administered intravenously, orally or a combination thereof during a preoperatively and/or intraoperative period and administered oral taurolidine, taurultam, one or more oxathiazin-like compounds, or a combination thereof postoperatively.

In one aspect, the patient is treated with C-2250 administered intravenously, orally or a combination thereof.

In one aspect, the patient is treated with C-2250 administered intravenously, orally or a combination thereof during a preoperatively and/or intraoperative period and administered oral C-2250 postoperatively.

In one aspect, the patient is treating with taurolidine, taurultam, one or more oxathiazin-like compounds, or a combination thereof in combination with one or more cyclin-dependent kinase (CDK) inhibitors. Any CDK inhibitor that is known in the field may be used in combination therapy. In one embodiment, CDK 4/6 inhibitors may be particularly useful. For example, palbociclib (PD-0332991), ribociclib (LEE011), and/or abemaciclib (LY2835219) may be used. In other embodiments, inhibitors of other CDKs may be used, e.g., dinaciclib (SCH-727965), a CDK ⅕ inhibitor may be used.

In one aspect, the patient is treating with taurolidine, taurultam, one or more oxathiazin-like compounds, or a combination thereof in combination with one or more hormone therapy drugs including anastrozole, letrozole, and tamoxifen. In some aspects, where the patient is a post-menopausal patient, the patient is treated with a anastrozole and/or letrozole in combination with taurolidine, taurultam, one or more oxathiazin-like compounds, or a combination thereof. In some aspects, where the patient is a pre-menopausal patient, the patient is treated with a tamoxifen in combination with taurolidine, taurultam, one or more oxathiazin-like compounds, or a combination thereof.

The present disclosure is also directed to a method of treating a patient suffering from TNBC by a multidisciplinary method involving treating the patient with a plurality of the following treatments: i) one or more checkpoint inhibitors; ii) hyperthermia treatment; iii) low dose chemotherapy; iv) Interleukin-2 (IL-2); and v) a compound selected from the group consisting of taurolidine, taurultam, oxathiazin-like compounds, and combinations thereof.

In one aspect, a patient suffering from TNBC is treated with the following treatments: i) one or more checkpoint inhibitors; ii) hyperthermia treatment; iii) low dose chemotherapy; iv) Interleukin-2 (IL-2); and v) a compound selected from the group consisting of taurolidine, taurultam, oxathiazin-like compounds, and combinations thereof.

In one aspect, a patient suffering from TNBC is treated sequentially with a plurality of the following treatments: i) one or more checkpoint inhibitors; ii) hyperthermia treatment; iii) low dose chemotherapy; iv) Interleukin-2 (IL-2); and v) a compound selected from the group consisting of taurolidine, taurultam, oxathiazin-like compounds, and combinations thereof.

In one aspect a patient suffering from TNBC is treated sequentially with the following treatments: i) one or more checkpoint inhibitors; ii) hyperthermia treatment; iii) low dose chemotherapy; iv) Interleukin-2 (IL-2); and v) a compound selected from the group consisting of taurolidine, taurultam, oxathiazin-like compounds, and combinations thereof.

In one aspect, a patient suffering from TNBC is treated with the following treatments: i) one or more checkpoint inhibitors; ii) hyperthermia treatment; iii) low dose chemotherapy; iv) Interleukin-2 (IL-2); and v) a compound selected from the group consisting of taurolidine, taurultam, oxathiazin-like compounds, and combinations thereof, wherein at least two of the treatments are carried out simultaneously or in tandem.

In one aspect, the one or more checkpoint inhibitors are administered in low doses.

In one aspect, IL-2 is administered at the biologically effective dose, the maximum tolerated dose, or at a dose between the biologically effective dose and the maximum tolerated dose.

Conventional chemotherapies target one of the three receptors (estrogen receptor (ER), progesterone receptor (PR) or Her2/neu (HER2)). In contrast, the present disclosure involves treating TNBC using taurolidine, taurultam, oxathiazin-like compounds, and combinations thereof, because these compounds are unexpectedly broad-spectrum therapeutics that can kill TNBC cells despite their heterogeneous nature as well as cancer stem cells.

BRIEF DESCRIPTION OF THE DRAWINGS

In the figures: *$p<0.05$, $p<0.01$, *$p<0.005$, ****$p<0.001$.

DETAILED DESCRIPTION OF THE INVENTION

Throughout this description all ranges described include all values and sub-ranges therein, unless otherwise specified. Additionally, the indefinite article "a" or "an" carries the meaning of "one or more" throughout the description, unless otherwise specified.

One aspect of the present disclosure is a method of treating a patient suffering from triple negative breast cancer (TNBC) comprising treating the patient with taurolidine, taurultam, one or more oxathiazin-like compounds, or a combination thereof, or treating the patient with a plurality of treatments selected from the group consisting of one or more checkpoint inhibitors, hyperthermia, low dose chemotherapy, and Interleukin-2 (IL-2) co-therapy with a compound selected from the group consisting of taurolidine, taurultam, one or more oxathiazin-like compounds, and combinations thereof.

In one aspect, the patient is treated with taurolidine, taurultam, one or more oxathiazin-like compounds, or a combination thereof administered intravenously, orally or a combination thereof.

In one aspect, the patient is treated with taurolidine, taurultam, one or more oxathiazin-like compounds, or a combination thereof administered intravenously, orally or a combination thereof during a preoperatively and/or intraoperative period and administered oral taurolidine, taurultam, one or more oxathiazin-like compounds, or a combination thereof postoperatively.

In one aspect, the patient is treated with C-2250 administered intravenously, orally or a combination thereof.

In one aspect, the patient is treated with C-2250 administered intravenously, orally or a combination thereof during a preoperatively and/or intraoperative period and administered oral C-2250 postoperatively.

In one aspect, the patient is treating with taurolidine, taurultam, one or more oxathiazin-like compounds, or a combination thereof in combination with one or more hormone therapy drugs including anastrozole, letrozole, and tamoxifen. In some aspects, where the patient is a postmenopausal patient, the patient is treated with a anastrozole and/or letrozole in combination with taurolidine, taurultam, one or more oxathiazin-like compounds, or a combination thereof. In some aspects, where the patient is a pre-menopausal patient, the patient is treated with a tamoxifen in combination with taurolidine, taurultam, one or more oxathiazin-like compounds, or a combination thereof. In certain embodiments, the combination of hormone therapy drugs with taurolidine, taurultam, one or more oxathiazin-like compounds, or a combination thereof includes a further combination with an anti-cancer drug, e.g., one or more of IL-2, cyclophosphamide, gemcitabine, 5-fluorouracil, paclitaxel, cisplatin, and carboplatin.

Figure 9:
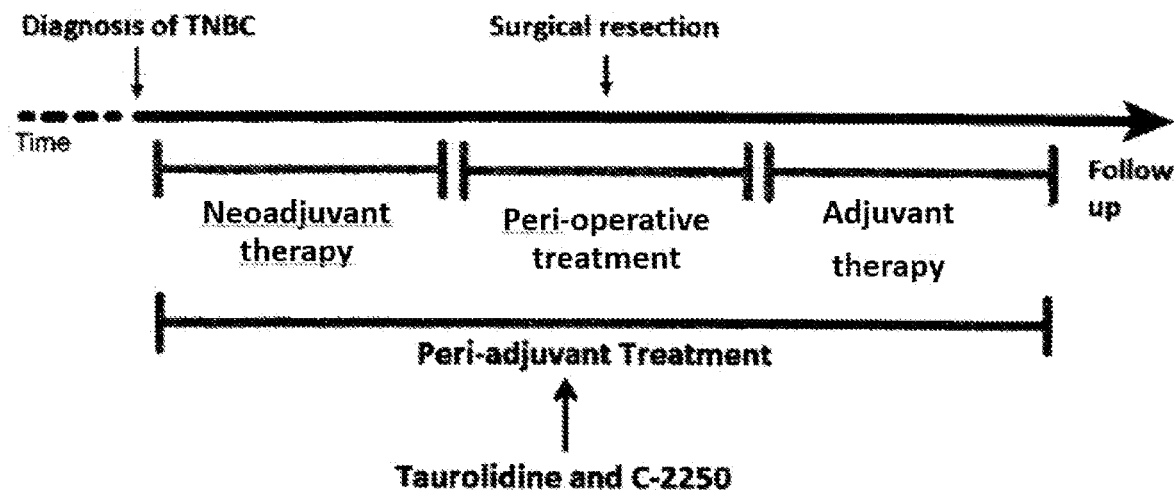
FIG. 9 schematically shows the use of taurolidine and/or C-2250 as a peri-adjuvant treatment of a subject diagnosed with TNBC.

According to certain embodiments, the present disclosure relates to a method of treating a patient suffering from TNBC by a multidisciplinary method involving treating the patient with one or more checkpoint inhibitors, hyperthermia, Interlekin-2 (IL-2) and a compound selected from the group consisting of taurolidine, taurultam, oxathiazin-like compounds, and combinations thereof. In certain embodiments, taurolidine and/or C-2250 can be used as a periadjuvant treatment of a subject diagnosed with TNBC as shown in FIG. 9.

Oxathiazin-like compounds are described in PCT/IB2015/059741, filed Dec. 17, 2015, which is incorporated herein by reference in its entirety.

One aspect of the present disclosure is directed to a method of treating a patient suffering from TNBC by a multidisciplinary method involving treating the patient with a plurality of the following treatments: i) one or more checkpoint inhibitors; ii) hyperthermia treatment; iii) low dose chemotherapy; iv) Interleukin-2 (IL-2); and v) a compound selected from the group consisting of taurolidine, taurultam, oxathiazin-like compounds, and combinations thereof.

In one aspect, a patient suffering from TNBC is treated with the following treatments: i) one or more checkpoint inhibitors; ii) hyperthermia treatment; iii) low dose chemotherapy; iv) Interleukin-2 (IL-2); and v) a compound selected from the group consisting of taurolidine, taurultam, oxathiazin-like compounds, and combinations thereof.

In one aspect, a patient suffering from TNBC is treated sequentially with a plurality of the following treatments: i) one or more checkpoint inhibitors; ii) hyperthermia treatment; iii) low dose chemotherapy; iv) Interleukin-2 (IL-2); and v) a compound selected from the group consisting of taurolidine, taurultam, oxathiazin-like compounds, and combinations thereof.

In one aspect a patient suffering from TNBC is treated sequentially with the following treatments: i) one or more checkpoint inhibitors; ii) hyperthermia treatment; iii) low dose chemotherapy; iv) Interleukin-2 (IL-2); and v) a compound selected from the group consisting of taurolidine, taurultam, oxathiazin-like compounds, and combinations thereof.

In one aspect, a patient suffering from TNBC is treated with the following treatments: i) one or more checkpoint inhibitors; ii) hyperthermia treatment; iii) low dose chemotherapy; iv) Interleukin-2 (IL-2); and v) a compound selected from the group consisting of taurolidine, taurultam, oxathiazin-like compounds, and combinations thereof, wherein at least two of the treatments are carried out simultaneously or in tandem.

In one aspect, the patient is co-administered IL-2 with a compound selected from the group consisting of taurolidine, taurultam, oxathiazin-like compounds, and combinations thereof. In certain embodiments, IL-2 is co-administered with taurolidine. In certain embodiments, IL-2 is co-administered with C-2250.

In one aspect, hyperthermia treatment involves locoregional hyperthermia, whole body hyperthermia (WBHT), or a sequential combination thereof, e.g., at a temperature range of 40 to 45° C., e.g., 40, 40.5, 41, 41.5, 42, 42.5, 43, 43.5, 44, 44.5 or 45° C. In certain embodiments, the hyperthermia treatment involves using a radiofrequency device for selective hyperthermia treatment.

In one embodiment, the method of this disclosure reduces or abrogates the proliferative ability of TNBC cells or cancer stem cells.

In one aspect, the one or more checkpoint inhibitors are administered in low doses. For example, the patient is administered two or three different checkpoint inhibitors simultaneously or sequentially during the treatment. In one aspect, the one or more checkpoint inhibitors are administered at a dose below a Food and Drug Administration (FDA) approved dosage amount. Checkpoint inhibitors include, but are not limited to human programmed death receptor-1 (PD-1) blocking antibodies and human cytotoxic T-lymphocyte antigen 4 (CTLA-4)-blocking antibodies. Checkpoint inhibitors include, but are not limited to nivolumab, ipilimumab, pembrolizumab, tremelimumab, and pidilizumab.

Low doses of checkpoint inhibitors include 0.1-1.8 mg/kg, 0.2-1.5 mg/kg, 0.4-1 mg/kg, or 0.5 mg/kg weekly, every two weeks, or every three weeks. Low doses of Nivolumab are: 0.1-1.8 mg/kg, 0.2-1.5 mg/kg, 0.4-1 mg/kg, or 0.5 mg/kg weekly, every two weeks, or every three weeks. Low doses of ipilimumab are: 0.1-1.8 mg/kg, 0.2-1.5 mg/kg, 0.3-1 mg/kg, or 0.3 mg/kg weekly, every two weeks, or every three weeks. Low doses of pembrolizumab are: 0.05-1.5 mg/kg, 0.1-1 mg/kg, 0.2-0.8 mg/kg, 0.3-0.5 mg/kg, or 0.2, 0.3, or 0.4 mg/kg weekly, every two weeks, or every three weeks.

In certain embodiments, the method of this disclosure includes follow-up monitoring by measuring circulating tumor cells (CTCs). CTCs are a subpopulation of tumor cells derived from the primary cancer site and circulating in the blood. The method of the present disclosure includes various strategies to enrich, detect and analyze these cells including PCR, e.g., real-time PCR (RT-PCR), multiplex PCR, RNA purification from blood, antibody-based capture methods (using key markers CK, EpCAM, BerEP4), and microfiltration methods. CTC counts may be incorporated in between, before or after any step of the method of this disclosure. In some embodiments, where CTC counts are above a pre-determined threshold, the method includes dosages of one or more of anti-cancer drugs in 1.5- to 2-fold increased amounts. Where CTC counts are below a pre-determined threshold, the method includes dosages of one or more of anti-cancer drugs 0.1 to 0.8 fold amounts, or non-administration of any of IL-2 and other anti-cancer drugs.

Chemotherapy utilizes anti-tumor agents to prevent cancer cells from multiplying, invading and metastasizing. As used herein, "low dose chemotherapy" refers to administration of anti-cancer pharmaceutical compounds at sub-therapeutic doses, i.e., lower than conventionally accepted doses for treatment of cancer when the pharmaceutical compound is administered by conventional means. Several drugs are available to treat breast cancer, including cytotoxic drugs such as doxorubicin, cyclophosphamide, methotrexate, paclitaxel, thiotepa, mitoxantrone, vincristine, or combinations thereof. Endocrine therapy may be an effective treatment where the remaining breast tissue retains endocrine sensitivity. Agents administered for this therapy include tamoxifen, megestrol acetate, aminoglutethimide, fluoxymesterone, leuprolide, gosserelin, and prednisone. In certain embodiments, the method includes using anti-cancer pharmaceutical compounds that down-regulate TReg cells. Such compounds include, but are not limited to cyclophosphamide, gemcitabine, 5-fluorouracil, paclitaxel, cisplatin, and carboplatin. Low dose chemotherapy includes, but is not limited to, administration of anti-tumor agents, e.g., cyclophosphamide, at doses of 100-800 mg/m$^2$, 200-500 mg/m$^2$ or 300 mg/m$^2$.

In one aspect, IL-2 is administered at an effective dose, the maximum tolerated dose, or at a dose between an effective dose and the maximum tolerated dose. Effective daily dosage amounts of IL-2 may include pharmaceutical dosage units within the range of 1,000,000,000 units (U) IL-2 per m$^2$ body surface area. Dosage amounts of IL-2 also may be found within the range of 100,000-1,000,000 U per kilogram body weight. Dosage amounts of IL-2 further may be found within the range of 0.1-100 micrograms IL-2 per kilogram body weight.

In certain embodiments, IL-2 is administered at a dose between 10 and 100 Mio I.U./m$^2$. In certain embodiments, IL-2 is administered at a dose between 18 and 75 Mio I.U./m$^2$. In certain embodiments, IL-2 is administered at a dose between 25 and 60 Mio I.U./m$^2$. In certain embodiments, IL-2 is administered at a dose of 54 Mio I.U./m$^2$.

Interleukin-2 (IL-2) is an agent which has been suggested for inhibiting tumor cell growth. However, administration of IL-2 to patients presents severe toxicity problems, since IL-2 elicits an extremely strong systemic inflammatory response syndrome (SIRS) reaction in patients. Toxicity of IL-2 is so severe that approximately 70% of patients cannot tolerate treatment. As used herein, "IL-2" includes natural or recombinant Interleukin-2, or biologically active derivatives or substantial equivalents thereof.

As described in U.S. Pat. No. 7,892,530 (Redmond and Pfirrmann), which his incorporated herein by reference in its entirety, methylol transfer agents such as taurolidine and taurultam reduce or substantially eliminate the severe toxicity and side effects of IL-2 in a combination therapy for inhibiting tumor metastases and treating cancer in patients, while it has unexpectedly been found that the efficacy of IL-2 is actually enhanced by the methylol transfer agents in the combination therapy of the present invention.

In certain embodiments, oxathiazin-like compounds according to formula I are utilized according to the invention wherein R is H, alkyl, or the like, such as methyl, ethyl, propyl, (e.g., isopropyl), benzyl or the like.

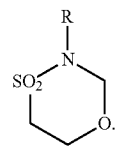

Formula I

In certain embodiments, C-2250 (Tetrahydro1,4,5-oxathiazin-4-dioxide or 1,4,5-oxathiazan-4-dioxide) is used.

The amount of the compounds needed depends on tumor size. In one embodiment, the invention includes surgically reducing tumor size and treating with one or more of the compounds. The compound may be administered before, during or after surgery to reduce tumors. Compounds according to the invention can be administered by any suitable method, including without limitation, by gels, capsules, tablets, IV, IP and/or directly to the tumor.

Gels can contain for example 2-4% (e.g., 3%) active compound of the invention, such as compound 2250, alone or in combination with taurolidine/taurultam which also can be administered and present alone, and can be for topical administration. Such gels can be used to treat tumors of the skin and mouth, including squamous cell tumors of the mouth and skin. Such gels also can be used to treat cervical cancer or cervical dysplasia by being administered in a suppository to the vagina, or by syringe. The invention may include the combination of a suppository carrying an active compound.

Solid dosage forms for oral administration include capsules, tablets, pills, powders, and granules. In such solid dosage forms, the provided composition is mixed with at least one inert, pharmaceutically acceptable excipient and/or fillers or extenders (e.g., starches, lactose, sucrose, glucose, mannitol, and silicic acid), binders (e.g., carboxymethylcellulose, alginates, gelatin, polyvinylpyrrolidinone, sucrose, and acacia), humectants (e.g., glycerol), disintegrating agents (e.g., agar, calcium carbonate, potato starch, tapioca starch, alginic acid, certain silicates, and sodium carbonate), solution retarding agents (e.g., paraffin), absorption accelerators (e.g., quaternary ammonium compounds), wetting agents (e.g., cetyl alcohol and glycerol monostearate), absorbents (e.g., kaolin and bentonite clay), and lubricants (e.g., talc, calcium stearate, magnesium stearate, solid polyethylene glycols, sodium lauryl sulfate), and mixtures thereof. In the case of capsules, tablets and pills, the dosage form may comprise buffering agents.

The compounds of this disclosure, particularly compound 2250, have been found to be very soluble in water. In certain embodiments, no PVP necessary to increase the solubility. For example, a 3.2% solution 2250 is isotonic. This is an unexpected advantage over taurolidine.

Compounds of the invention, such as compound 2250 (with or without taurolidine and/or taurultam) are particularly useful in surgical oncology, since the compounds do not hinder wound healing. Administration of other antineoplastic drugs must be delayed for up to five weeks or more after surgery because other such antineoplastic drugs hinder wound healing and promote anastomotic leakage. Such problems can be avoided with compounds of the invention such as compound 2250, which can be administered during surgery and immediately thereafter, without wound healing issues or leakage issues.

Solid compositions of a similar type may be employed as fillers in soft and/or hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the provided composition(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

In certain embodiments, capsules may contain an excipient formulation containing one or more of hydroxypropyl methylcellulose (HPMC), gelatin, and fish gelatin. In certain embodiments, a capsule may contain compound 2250 in combination with taurolidine and/or taurultam. The capsule may optionally further contain one or more of lycopene, ellagic acid (polyphenol), curcumin, piperine, delphinidin, resveratrol, isothiocyanates such as sulforaphane, capsaicin, and piperlongumine.

Active compounds of the invention, such as compound 2250, can be combined with compounds such as gemcitabine. This combination can be used to treat cancers, such as pancreatic cancer. Taurolidine and/or taurultam also can be combined with gemcitabine to treat, for example, pancreatic cancer.

In some embodiments, a nutritional cancer prophylaxis and treatment product may contain 100-500 mg compound 2250 alone or in combination with 100-500 mg taurolidine and/or taurultam and one or more of lycopene, e.g., 20-200 mg, ellagic acid (polyphenol), curcumin, piperine (20-200 mg), delphinidin, resveratrol, isothiocyanates such as sulforaphane, capsaicin, and piperlongumine.

It was unexpectedly found that the compounds could be administered during surgery and immediately after surgery because the compounds do not inhibit wound healing like other chemotherapy agents.

It was unexpectedly found that taurolidine, taurultam, and oxathiazin-like compounds and derivatives thereof kill tumor stem cells, which is very unusual and perhaps unknown among chemotherapy agents. Typical chemotherapy agents, if effective against tumor stem cells, generally are only effective at very high doses which are extremely toxic to human patients.

It was unexpectedly found that lower doses of taurolidine and/or taurultam killed tumor stem cells than were needed to kill tumor cells.

Oxathiazin-like compounds and derivatives thereof have a half-life in human blood that is significantly longer than the half-life of taurolidine and taurultam. Accordingly, these compounds are cleared less rapidly from the bloodstream of the patients, thereby effectively delaying loss of drug potency caused by the body's clearance mechanisms.

The Oxathiazin-like compounds have reduced burning sensation when applied directly into tissue, unlike this effect observed in patients treated with taurolidine.

The Oxathiazin-like compounds have a particularly advantageous combination of properties including high water solubility, versatile administration routes including oral and i.v., extended stability and half-life, and significantly reduced side effect of burning sensation. The reduced burning sensation makes the oxathiazin-like compounds including 2250 very suitable for pharmaceutical uses including oral, peripheral, i.v., i.p., and other administration methods in which the patient could suffer from a burning sensation.

Another significant advantage is that the half-life of compound 2250 is greater than 24 hours in human blood, which is significantly higher than the half-life of taurolidine, which was found to be ~30 minutes using the same test.

The daily dosage may be about 0.1 g to about 100 g, e.g., about 5 g to about 30 g. The daily dosage may be administered in the form of an orally administrable composition. The daily dosage may be administered in the form of a capsule, a tablet, or a pharmaceutically acceptable solution. The daily dosage may be administered in a form that contains compound 2250 at a concentration of about 0.01 to about 3% w/v. The daily dosage may be administered in a form that contains compound 2250 at a concentration of about 0.01 µg/ml to about 1000 µg/ml. The daily dosage may be administered in a form that contains one or more solubilizing agents, e.g., polyols.

In some embodiments, the compounds are administered in compositions at a concentration of about 0.01 to about 1000 µg/ml. In some embodiments, the compounds are administered in compositions at a concentration of about 1 to about 100 µg/ml. In some embodiments, the compounds are administered in compositions at a concentration of about 10 to about 50 µg/ml. The composition may also contain about 0.01 to about 1000 µg/ml, about 1 to about 100 µg/ml, or about 10 to about 50 µg/ml taurolidine and/or taurultam.

In some embodiments, the compounds are administered in compositions at a concentration of about 0.01 to about 3%. In some embodiments, the compounds are administered in compositions at a concentration of about 0.1 to about 2.5%. In some embodiments, the compounds are administered in compositions at a concentration of about 1% to about 2%. The composition may additionally contain about 0.01 to about 3%, about 0.1 to about 2.5%, or about 1 to about 2% taurolidine and/or taurultam.

In one embodiment, the oxathiazin-like compounds and derivatives thereof may be administered as a co-therapy with taurolidine and/or taurultam to kill tumor stem cells. In accordance with such an embodiment, the co-therapy has been unexpectedly found to require a lower dosage of drug to kill tumor stem cells than necessary to kill normal tumor cells.

In certain embodiments, the oxathiazin-like compounds and derivatives thereof may be administered with Vitamin D3, which results to increase the anti-tumor effects of the compounds.

In certain embodiments, hyperthermia therapy may be co-administered with Vitamin C. In certain embodiments, the Vitamin C is high dose, e.g., 0.3-1 g/kg, or 0.5 g/kg.

In certain embodiments, hyperthermia therapy may be co-administered with alpha lipoic acid, e.g., at a dose of 500-1000 mg, 600 mg or 800 mg.

In one embodiment, taurolidine, taurultam, or oxathiazin-like compounds may be administered to the subject at a total daily dose of from about 0.1 g to about 100 g, about 1 g to about 80 g, about 2 g to about 50 g, or about 5 g to about 30 g.

Effective dosage amounts of taurolidine, taurultam, or oxathiazin-like compounds are dosage units within the range of about 0.1-1,000 mg/kg, preferably 150-450 mg/kg per day, and most preferably 300-450 mg/kg per day. Preferred dosages may be in the range of about 10-20 grams taurolidine, taurultam or a mixture thereof, per administration.

Other advantages of the use of taurolidine, taurultam, or oxathiazin-like compounds include avoidance of toxicity of conventional therapies, which make such therapies intolerable. Using the taurolidine, taurultam, or oxathiazin-like compounds for treating TNBC is advantageous for avoiding side effects of existing therapies including hair loss, thrush, burns from radiation, loss of appetite, infections, nausea, menopause, skin rash, tingling or numbness in hands and feet, hearing problems, loss of balance, joint pain, and swollen legs and feet.

In some embodiments, 2% taurolidine solution is administered by intravenous infusion about 1-6 times per day, more preferably about 2-4 times per day, during a treatment period, concurrently with administration of about 10,000,000-40,000,000 units m$^2$ IL-2 by intravenous infusion per day during the treatment period.

As used herein, the term pure refers to a substance that is at least about 80% pure of impurities and contaminants. In some embodiments, the term pure refers to a substance that is at least about 90% pure of impurities and contaminants. In certain embodiments, the term pure refers to a substance that is at least about 95% pure of impurities and contaminants. In some embodiments, the term pure refers to a substance that is at least about 99% pure of impurities and contaminants. In some embodiments, the term pure refers to a substance that is at least about 99.5% pure of impurities and contaminants.

In certain embodiments, compounds, compositions, and methods of the present invention encompass the use of micronized compounds. In some embodiments, the term "micronized" as used herein refers to a particle size in the range of about 0.005 to 100 microns. In certain embodiments, the term "micronized" as used herein refers to a particle size in the range of about 0.5 to 50 microns. In certain embodiments, the term "micronized" as used herein refers to a particle size in the range of about 1 to 25 microns. For example, the size of the drug particles may be about 1, 5, 10, 15, 20, or 25 microns.

In certain embodiments, compounds, compositions, and methods of the present invention encompass the use of nanoparticles. As used herein, the term "nanoparticle" refers to any particle having a diameter of less than 1000 nanometers (nm). In some embodiments, a nanoparticle has a diameter of less than 300 nm. In some embodiments, a nanoparticle has a diameter of less than 100 nm. In some embodiments, a nanoparticle has a diameter of less than 50 nm, e.g., between about 1 nm and 50 nm.

Suitable formulations for injection or infusion may comprise an isotonic solution containing one or more solubilizing agents, e.g., polyols such as glucose, in order to provide solutions of increased compound concentration. Such solutions are described in EP 25366261. The solution can be rendered isotonic with ringer solution or ringer lactate solution. The concentration of the compound in such solutions may be in the range 1-60 g/liter.

The compounds may be in crystalline form, e.g., after crystallization and/or recrystallization in an alcohol, ketone, ester, or combination thereof. For example, the compounds of the present invention may be crystallized and/or recrystallized from an alcohol such as ethanol.

Exemplary oxathiazin-like compounds include the following:

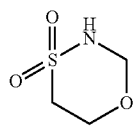
2250

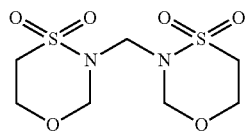
2245

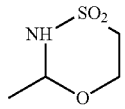
2256

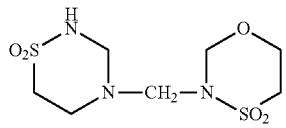
B1

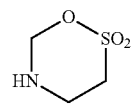
A1

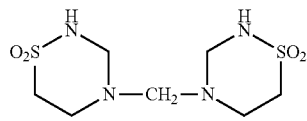
B2

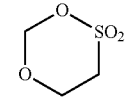
A3

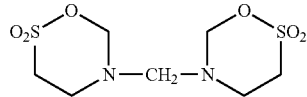
B3

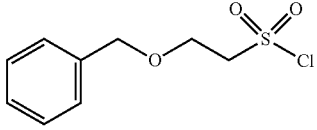
1906

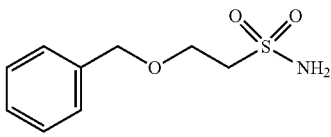
1907

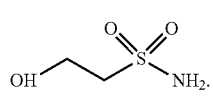
1908

It has been found that when used in the form of nanoparticles, the compounds of the claimed invention achieve higher blood levels. In one embodiment, the present invention includes compound 2250 alone or in combination with taurolidine and/or taurultam. For example, the present invention includes nanoparticles of the compounds of the present invention encapsulated in capsules.

In certain embodiments, the invention also relates to derivatives of the above compounds having, e.g., activity as described herein of said compounds, for example, at least 25%, 30%, 40%, 50%, 60%, 70%, 80%, 90%, 95%, 100%, or more, of said activity.

In certain embodiments, the invention also relates to compositions containing the compounds described herein, including pharmaceutically acceptable solutions of said compounds, as well as orally administrable compositions such as capsules and tablets containing said compositions.

In certain embodiments, this disclosure relates to administering of an oxathiazin-like compound orally to a patient. In some embodiments, an oxathiazin-like compound is formulated in capsules. In certain embodiments, capsules contain between 50-1000 mg of an oxathiazin-like compound. In certain embodiments, capsules contain between 100-500 mg of an oxathiazin-like compound. In certain embodiments, capsules contain between 200-400 mg of an oxathiazin-like compound. In certain embodiments, capsules contain between 250-350 mg of an oxathiazin-like compound. In certain embodiments, the oxathiazin-like compound is C-2250.

In certain embodiments, the present disclosure relates to a synergistic combination of IL-2 and C-2250, including combined drug formulations containing IL-2 and C-2250, as well as methods involving administering IL-2 and C-2250 simultaneously and/or concurrently, e.g., in separate or combined dosage forms. According to this co-therapy, the patient is protected from the toxic side effects of IL-2 monotherapy while benefiting from the anti-TNBC efficacies of both IL-2 and C-2250. The combination therapy unexpectedly increases the efficacy of the therapy compared to the additive effects of IL-2 and C-2250, thereby providing a synergistically increased efficacy. Moreover, the reduction in adverse effects compared to IL-2 monotherapy further unexpectedly bolsters the synergistic effects. In certain embodiments, the compounds of the present invention can be administered to a subject or patient by any suitable means, for example, in solution, e.g., locally, systemically such as by intravenous infusion, or the like.

In one embodiment, this disclosure includes a method of killing tumor stem cells by administering to a subject in need thereof a tumor stem cell killing effective amount of taurolidine, taurultam, or a mixture thereof. The tumor stem cell killing effective amount of taurolidine and/or taurultam is less than an amount of taurolidine and/or taurultam required for killing tumor cells.

In some embodiments, the taurolidine, taurultam, or a mixture thereof is administered in a tumor stem cell killing composition at a concentration of about 0.01 to about 500 µg/ml. In some embodiments, the taurolidine, taurultam, or a mixture thereof is administered in a tumor stem cell killing composition at a concentration of about 0.1 to about 100 µg/ml. In some embodiments, the taurolidine, taurultam, or a mixture thereof is administered in a tumor stem cell killing effective composition at a concentration of about 10 to about 50 µg/ml. Taurolidine is effective at killing tumor stem cells in tissue culture in vitro at 0.01 µg/ml.

In some embodiments, the taurolidine, taurultam, or a mixture thereof is administered in a tumor stem cell killing composition at a concentration of about 0.001 to about 2%. In some embodiments, the taurolidine, taurultam, or a mixture thereof is administered in a tumor stem cell killing composition at a concentration of about 0.01 to about 1.5%. In some embodiments, the taurolidine, taurultam, or a mixture thereof is administered in a tumor stem cell killing composition at a concentration of about 0.1% to about 1%.

In one embodiment, the taurolidine, taurultam, or a mixture thereof is administered for tumor stem cell killing to a subject in need thereof at a total daily dose of from about 0.01 g to about 50 g, about 0.1 g to about 30 g, about 0.5 g to about 10 g, or about 1 g to about 5 g.

Tumor stem cell killing effective dosage amounts of the taurolidine, taurultam, or a mixture thereof are dosage units within the range of about 0.01-500 mg/kg, preferably 1-100 mg/kg per day, and most preferably 5-50 mg/kg per day.

In another embodiment, this disclosure includes a method of killing tumor stem cells by administering to a subject in need thereof a compound selected from the following compounds:

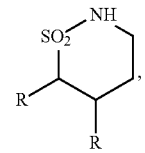

wherein each R is independently H, alkyl, or aryl,

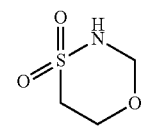
2250

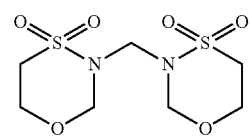
2245

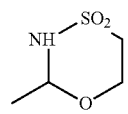
2256

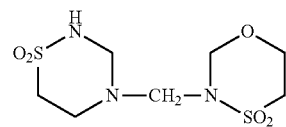
B1

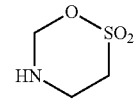
A1

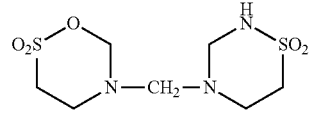
B2

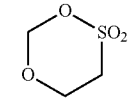
A3

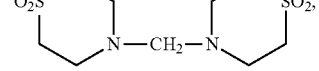
B3 which may be used in combination with taurolidine and/or taurultam. Such a technique provides a method for killing tumor stem cells using at least two compounds having different half-lives, and thereby broadening the pharmacokinetic effects obtained thereby. In one embodiment, compound 2250 may be used in combination with taurolidine and/or taurultam.

The present disclosure relates to the items described below.

Item 1. A method of treating a patient suffering from triple negative breast cancer (TNBC) comprising treating the patient with taurolidine, taurultam, one or more oxathiazin-like compounds, or a combination thereof, or treating the patient with a plurality of treatments selected from the group consisting of one or more checkpoint inhibitors, hyperthermia, low dose chemotherapy, and Interleukin-2 (IL-2) co-therapy with a compound selected from the group consisting of taurolidine, taurultam, one or more oxathiazin-like compounds, and combinations thereof.

Item 2. The method of item 1, wherein the patient is treated with taurolidine, taurultam, one or more oxathiazin-like compounds, or a combination thereof administered intravenously, orally or a combination thereof.

Item 3. The method of items 1-2, wherein the patient is treated with taurolidine, taurultam, one or more oxathiazin-like compounds, or a combination thereof administered intravenously, orally or a combination thereof during a preoperative and/or intraoperative period and administered oral taurolidine, taurultam, one or more oxathiazin-like compounds, or a combination thereof postoperatively.

Item 4. The method of items 1-3, wherein the patient is treated with C-2250 administered intravenously, orally or a combination thereof.

Item 5. The method of items 1-4, wherein the patient is treated with C-2250 administered intravenously, orally or a combination thereof during a preoperative and/or intraoperative period and administered oral C-2250 postoperatively.

Item 6. The method of items 1-5, wherein the oral dosage form of C-2250 is a capsule that, when ingested orally, achieves a blood level Cmax of ≥2 µg/ml.

Item 7. The method of items 1-6, wherein the oral dosage form of C-2250 is a capsule that, when ingested orally, achieves a blood level Cmax of ≥5 µg/ml.

Item 8. The method of items 1-7, wherein the oral dosage form of C-2250 is a capsule that, when ingested orally, achieves a blood level Cmax of ≥15 µg/ml.

Item 9. The method of items 1-8, comprising treating the patient with a plurality of treatments comprising administering C-2250 and IL-2 to the patient in an effective amount without inducing toxic side effects associated with IL-2 monotherapy.

Item 10. The method of item 1-9, wherein at least two of the treatments are carried out simultaneously or in tandem.

Item 11. The method of items 1-10, comprising treating the patient with all of the plurality of treatments.

Item 12. The method of items 1-11, comprising sequentially administering one or more checkpoint inhibitors to the patient, subjecting the patient to hyperthermia treatment, administering low dose chemotherapy to the patient, and co-administering IL-2 with a compound selected from the group consisting of taurolidine, taurultam, oxathiazin-like compounds, and combinations thereof.

Item 13. The method of items 1-12, wherein IL-2 is administered at the biologically effective dose, the maximum tolerated dose, or at a dose between the biologically effective dose and the maximum tolerated dose.

Item 14. The method of items 1-13, wherein IL-2 is administered at a dose between 25 and 60 Mio I.U./m².

Item 15. The method of items 1-14, wherein IL-2 is co-administered with taurolidine, taurultam or a combination thereof.

Item 16. The method of items 1-15, wherein IL-2 is co-administered with one or more of the following compounds:

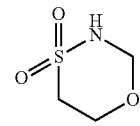
2250

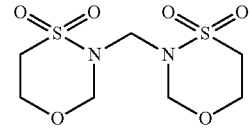
2245

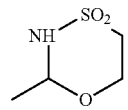
2256

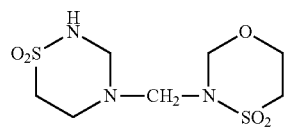
B1

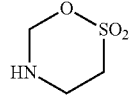
A1

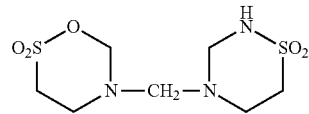
B2

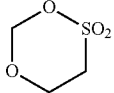
A3

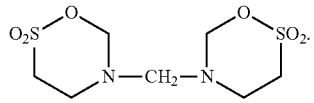
B3

Item 17. The method of items 1-16, wherein IL-2 is co-administered with C-2250

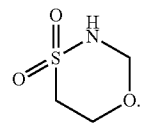

Item 18. The method of items 1-17, wherein the patient is administered hyperthermia treatment.

Item 19. The method of items 1-18, wherein the patient is administered loco-regional hyperthermia treatment.

Item 20. The method of items 1-19, wherein the patient is administered whole body hyperthermia (WBHT).

Item 21. The method of items 1-20, wherein the patient is administered a sequential combination of loco-regional and whole body hyperthermia treatment.

Item 22. The method of items 1-21, wherein the patient is administered one or more checkpoint inhibitors.

Item 23. The method of items 1-22, wherein the patient is administered two or three checkpoint inhibitors.

Item 24. The method of items 1-23, wherein the patient is simultaneously administered two checkpoint inhibitors.

Item 25. The method of items 1-24, wherein the one or more checkpoint inhibitors are administered at dosage amounts below Food and Drug Administration (FDA) approved dosage amounts for the one or more checkpoint inhibitors.

Item 26. The method of items 1-25, wherein the one or more checkpoint inhibitors are not human programmed death receptor-1 (PD-1) blocking antibodies and/or human cytotoxic T-lymphocyte antigen 4 (CTLA-4)-blocking antibodies.

Item 27. The method of items 1-26, wherein the one or more checkpoint inhibitors are selected from the group consisting of nivolumab, ipilimumab, pembrolizumab, tremelimumab, and pidilizumab.

Item 28. The method of items 1-27, wherein the one or more checkpoint inhibitors are nivolumab and ipilimumab.

Item 29. The method of items 1-28, wherein the one or more checkpoint inhibitors are administered at doses of 0.1-1.8 mg/kg weekly, every two weeks, or every three weeks.

Item 30. The method of items 1-29, wherein the one or more checkpoint inhibitors are administered at doses of 0.3-0.6 mg/kg weekly, every two weeks, or every three weeks.

Item 31. The method of items 1-30, wherein the patient is administered low dose chemotherapy.

Item 32. The method of items 1-31, wherein the patient is administered cyclophosphamide, gemcitabine, 5-fluorouracil, paclitaxel, cisplatin, and carboplatin.

Item 33. The method of items 1-32, wherein the low dose chemotherapy comprises administering 100-800 mg/m$^2$ of an anti-tumor agent.

Item 34. The method of items 1-33, wherein the low dose chemotherapy comprises administering an anti-tumor agent effective for down-modulating TReg cells in an amount effective for down-modulating, but below a cytotoxic level.

Item 35. The method of items 1-34, wherein said plurality of treatments does not induce intolerable side effects of conventional chemotherapy and IL-2 administration.

Item 36. The method of items 1-35, comprising administering IL-2 to the patient without inducing vascular leak syndrome in the patient.

Item 37. The method of items 1-36, comprising administering IL-2 to the patient without inducing hypotension and/or impaired renal function in the patient.

Item 38. The method of items 1-37, wherein the patient has a Karnofsky score improvement of 20% or more after the plurality of treatments are performed.

Item 39. The method of items 1-38, further comprising reducing neuropathy and/or neuropathic pain in the patient.

Item 40. The method of items 1-39, wherein the patient has increased appetite after the plurality of treatments are performed.

Item 41. The method of items 1-40, further comprising reducing insomnia in the patient.

Item 42. The method of items 1-41, further comprising reducing cachexia and/or fatigue in the patient.

Item 43. The method of items 1-42, further comprising administering vitamins to the patient.

Item 44. The method of items 1-43, further comprising administering Vitamin C to the patient.

Item 45. The method of items 1-44, further comprising administering alpha lipoic acid to the patient.

Item 46. The method of items 1-45, comprising administering IL-2 in combination with taurolidine to the patient for 5-7 days.

Item 47. The method of items 1-46, comprising administering PD-1 and CTLA-4 checkpoint inhibitors to the patient once weekly.

Item 48. The method of items 1-47, wherein the PD-1 and CTLA-4 checkpoint inhibitors are administered to the patient for 3-5 weeks.

Item 49. The method of items 1-48, comprising administering PD-1 and CTLA-4 checkpoint inhibitors to the patient and concurrently treating the patient with hyperthermia treatment.

Item 50. The method of items 1-49, wherein the hyperthermia treatment is administered to the patient for 3-5 weeks.

Item 51. The method of items 1-50, wherein the hyperthermia treatment is loco-regional hyperthermia treatment.

Item 52. The method of items 1-51, comprising administering low dose chemotherapy to the patient and concurrently treating the patient with hyperthermia treatment.

Item 53. The method of items 1-52, wherein the hyperthermia treatment is whole body hyperthermia treatment.

Item 54. The method of items 1-53, wherein the patient is treating with taurolidine, taurultam, one or more oxathiazin-like compounds, or a combination thereof in combination with one or more hormone therapy drugs.

Item 55. The method of items 1-54, wherein the hormone therapy drug is anastrozole, letrozole, and/or tamoxifen.

Item 56. The method of items 1-55, wherein the patient is post-menopausal and is treated with anastrozole and/or letrozole in combination with taurolidine, taurultam, one or more oxathiazin-like compounds, or a combination thereof.

Item 57. The method of items 1-56, wherein the patient is post-menopausal and the patient is treated with a tamoxifen in combination with taurolidine, taurultam, one or more oxathiazin-like compounds, or a combination thereof.

Item 58. The method of items 1-57, wherein the combination of hormone therapy drugs with taurolidine, taurultam, one or more oxathiazin-like compounds, or a combination thereof further comprising administering an anti-cancer drug.

Item 59. The method of items 1-58, wherein the anti-cancer drug is one or more of IL-2, cyclophosphamide, gemcitabine, 5-fluorouracil, paclitaxel, cisplatin, and carboplatin.

Item 60. The method of items 1-59, wherein the oxathiazin-like compound is C-2250.

Item 61. The method of items 1-60, wherein the patient is administered one or more cyclin-dependent kinase (CDK) inhibitor.

Item 62. The method of items 1-61, wherein the CDK inhibitor is a CDK 4/6 inhibitor.

Item 63. The method of items 1-61, wherein the CDK inhibitor is palbociclib, ribociclib, abemaciclib, dinaciclib, or a combination thereof.

EXAMPLES

Example 1: Breast Cancer Cell Viability Studies

Introduction

Based on the recognition of taurolidine and C-2250 as powerful anti-neoplastic agents, these agents were tested against the following breast cancer cell lines: BT-20 (primary breast cancer, HR negative), MDA-MB-231 (metastatic, HR negative) and MCF-7 (metastatic, HR positive). BT-20 and MDA-MB-231 are TNBC cell lines, whereas MCF-7 is not a TNBC cell line.

Material and Methods

The BT-20 cell lines were cultured in EMEM supplemented with 10% fetal bovine serum (FBS) and 1% penicillin-streptomycin (pen-strep). The MCF-7 was cultured in DMEM, supplemented with 10% FBS, 1% pen-strep and 0.1% Insulin. The MDA-MB-231 was cultured in DMEM with 10% FBS and 1% pen-strep. All cells were cultured at 37° C. in a humidified atmosphere with 5% $CO_2$.

Chemicals: Taurolidine 2% solution and C-2250 ultra-pure powder were provided by Geistlich Pharma AG, Wolhusen, assignee of the present invention. The C-2250 solution was prepared by dissolving it in the PBS solution to final concentration. The reagents were further diluted into 5 five different concentrations, with taurolidine at 10, 100, 250, 500 and 1000 µM, while the C-2250 was diluted into 100, 250, 500, 750 and 1000 µM.

Colony forming assay: 100 µl of breast cancer cell lines were seeded in 96-well plates at their respective optimal density (BT-20 and MDA-MB-231: $1.0\times10^5$ cells/ml; BT-474: $5.0\times10^5$ cells/ml; and MCF-7: $0.5\times10^5$ cells/ml). Cells were incubated under culture condition for 12 hours to allow the cells to adhere. Culture medium was then removed and fresh culture medium alone (control) or culture medium with different concentrations of taurolidine (10, 100, 250, 500 and 1000 µM) and C-2250 (100, 250, 500, 750 and 1000 µM) were added.

Cell viability assays: After 24 hours, 10 µl of MTT solution was added into each well and incubation was protracted for another 2 hours. The supernatant was then removed, washed with 100 µl PBS before 100 µl DMSO was added. Absorbance was measured using a Microtitre Plate Reader (Dynex Technologies Inc., Chantilly, Va.) at 570 nm wavelength. The experiment was performed also at 48 hours and the entire procedure was repeated 3 times.

Results

Data are expressed as the mean±SEM and are representative of three separate experiments.

Figure 1A:
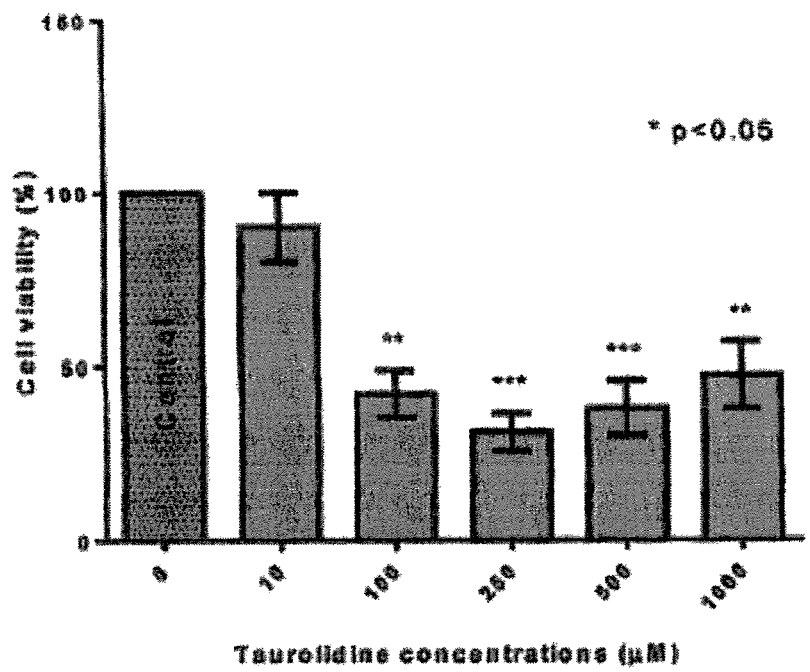
FIG. 1A graphically shows the effects of different concentrations of taurolidine on cell viability of BT-20 cell lines after 24 hours.
Figure 1B:
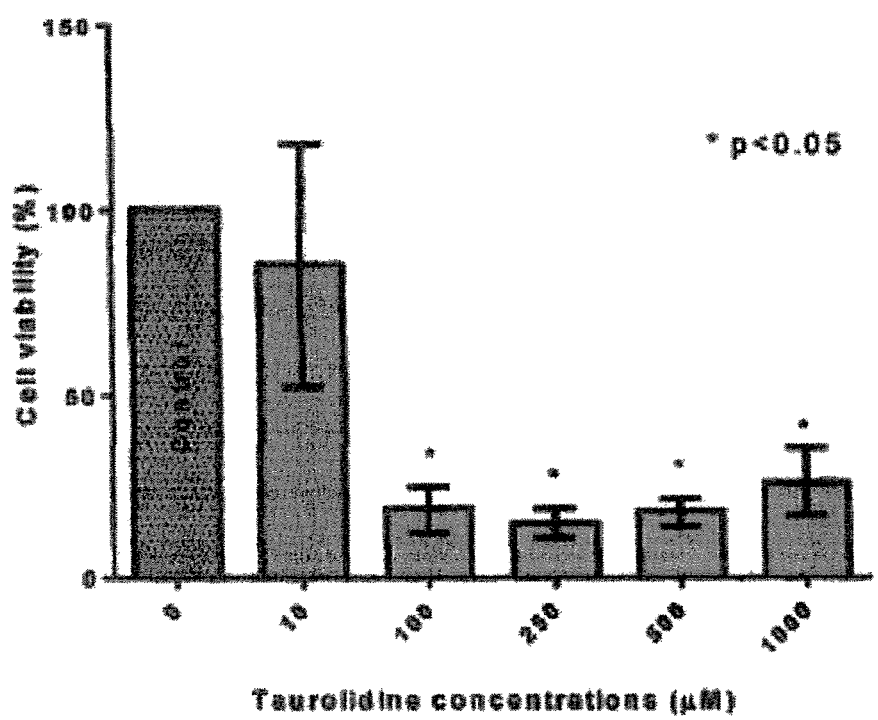
FIG. 1B graphically shows the effects of different concentrations of taurolidine on cell viability of BT-20 cell lines after 48 hours.

The results of the cell viability studies for taurolidine on cell viability of BT-20 cell lines after 24 and 48 hours are shown in FIGS. 1A and 1B.

Figure 2A:
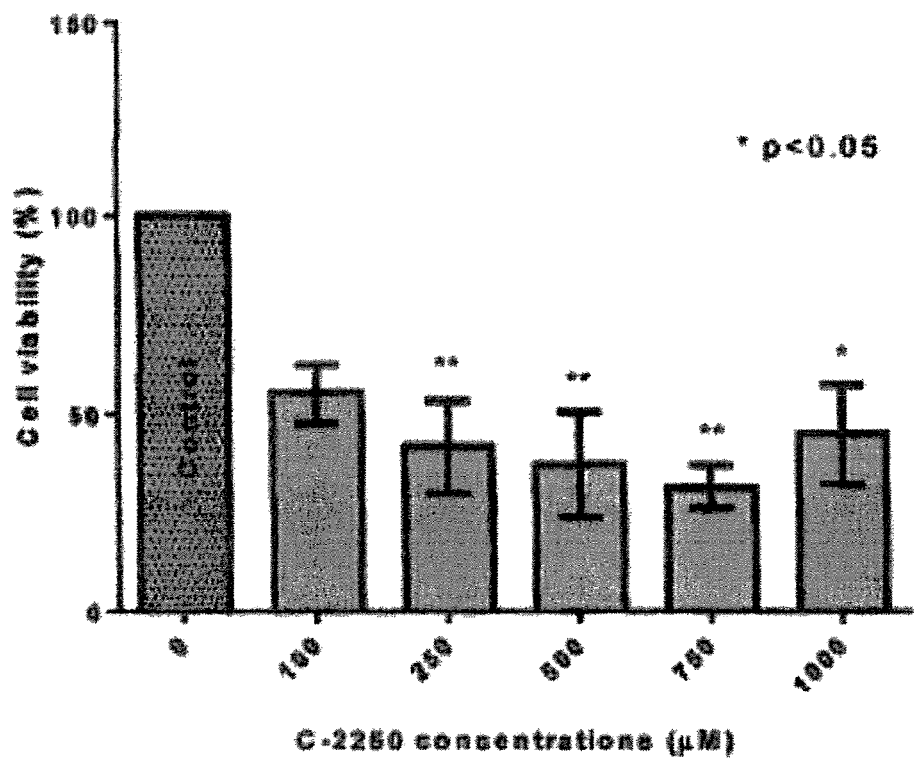
FIG. 2A graphically shows the effects of different concentrations of C-2250 on cell viability of BT-20 cell lines after 24 hours.
Figure 2B:
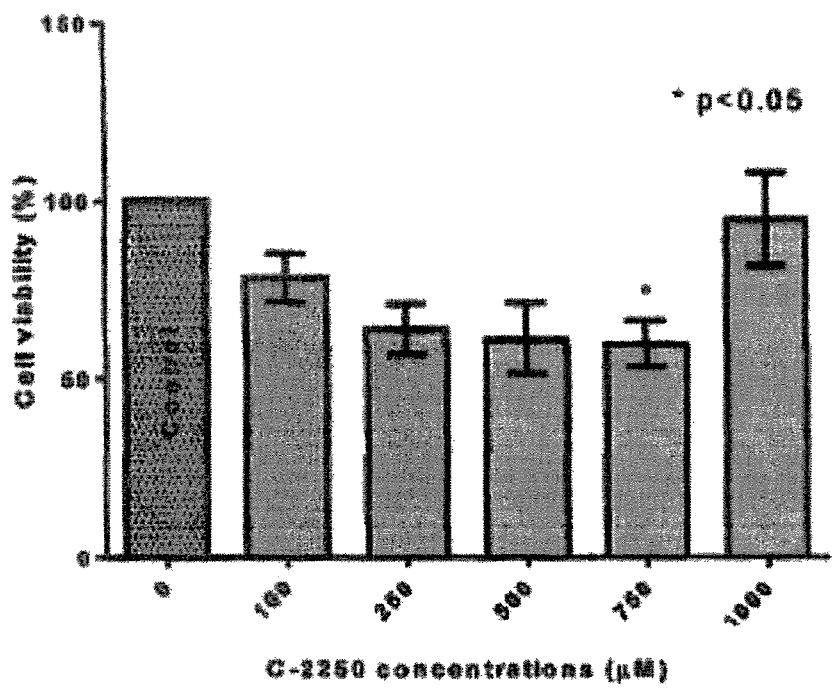
FIG. 2B graphically shows the effects of different concentrations of C-2250 on cell viability of BT-20 cell lines after 48 hours.

The results of the cell viability studies for C-2250 on cell viability of BT-20 cell lines after 24 and 48 hours are shown in FIGS. 2A and 2B.

Figure 3A:
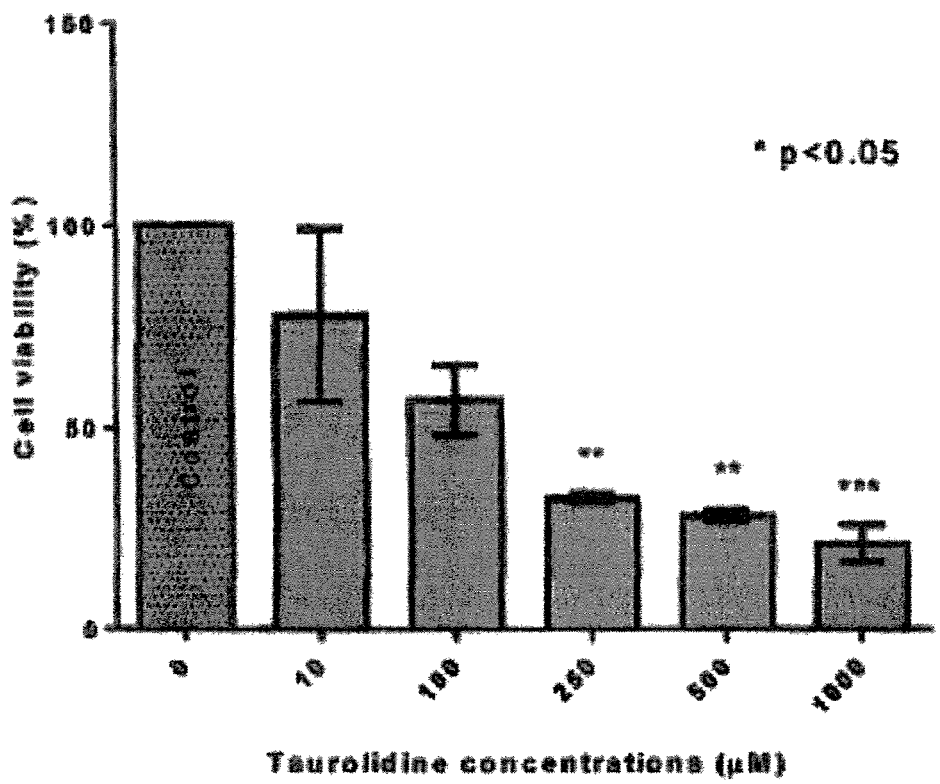
FIG. 3A graphically shows the effects of different concentrations of taurolidine on cell viability of MCF-7 cell lines after 24 hours.
Figure 3B:
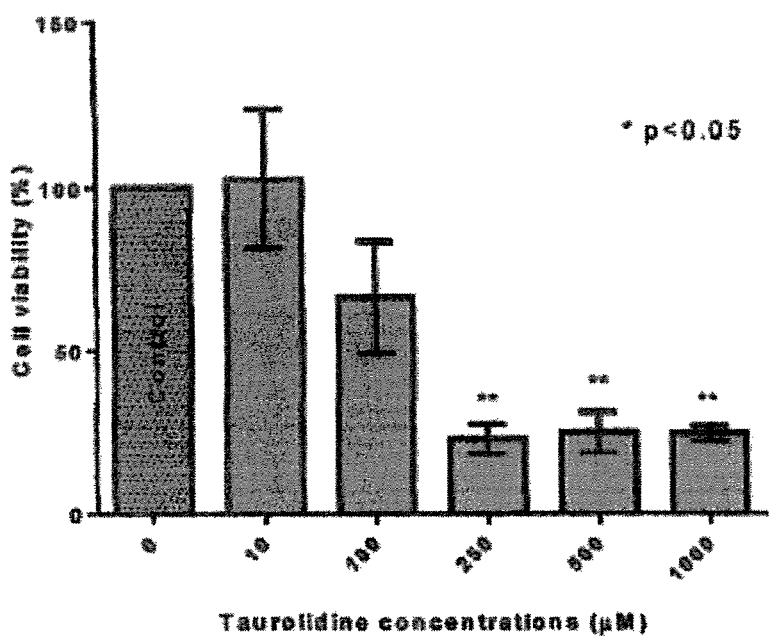
FIG. 3B graphically shows the effects of different concentrations of taurolidine on cell viability of MCF-7 cell lines after 48 hours.

The results of the cell viability studies for taurolidine on cell viability of MCF-7 cell lines after 24 and 48 hours are shown in FIGS. 3A and 3B.

Figure 4A:
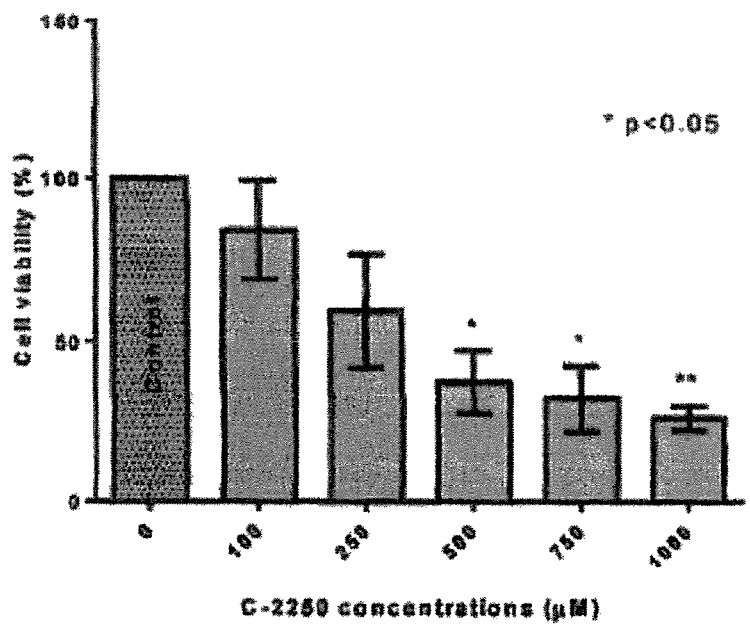
FIG. 4A graphically shows the effects of different concentrations of C-2250 on cell viability of MCF-7 cell lines after 24 hours.
Figure 4B:
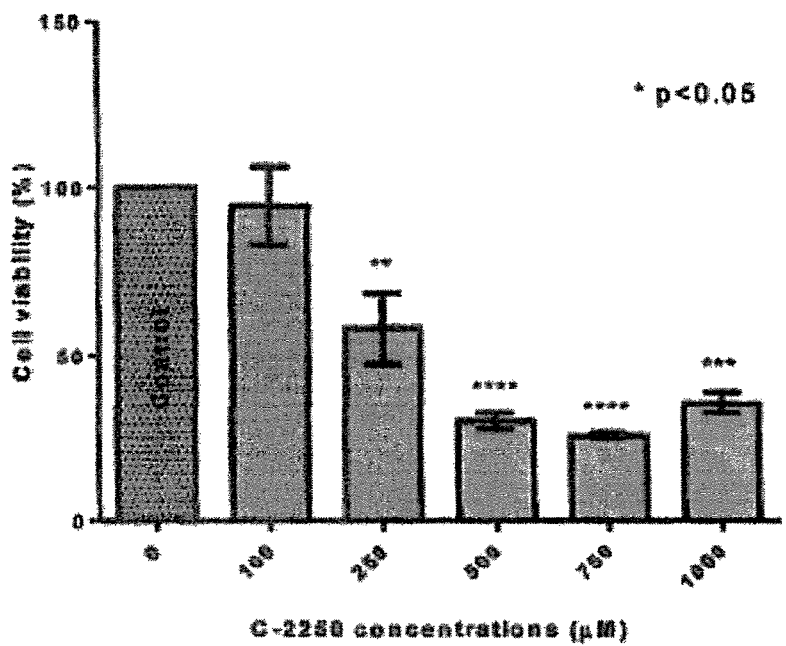
FIG. 4B graphically shows the effects of different concentrations of C-2250 on cell viability of MCF-7 cell lines after 48 hours.

The results of the cell viability studies for C-2250 on cell viability of MCF-7 cell lines after 24 and 48 hours are shown in FIGS. 4A and 4B.

Figure 5A:
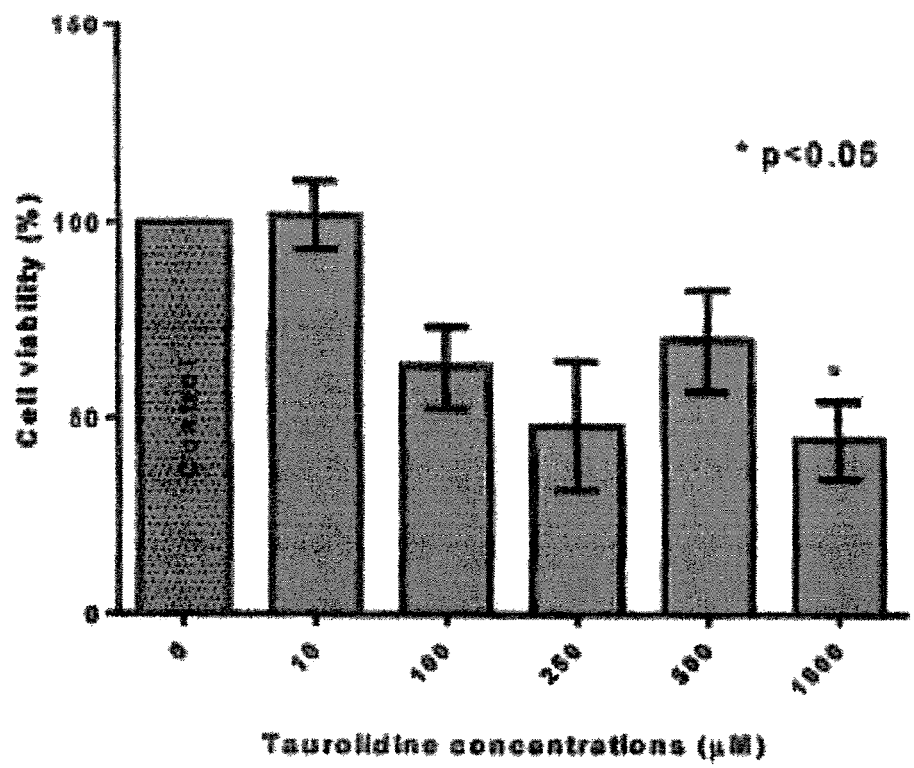
FIG. 5A graphically shows the effects of different concentrations of taurolidine on cell viability of MDA-MB-231 cell lines after 24 hours.
Figure 5B:
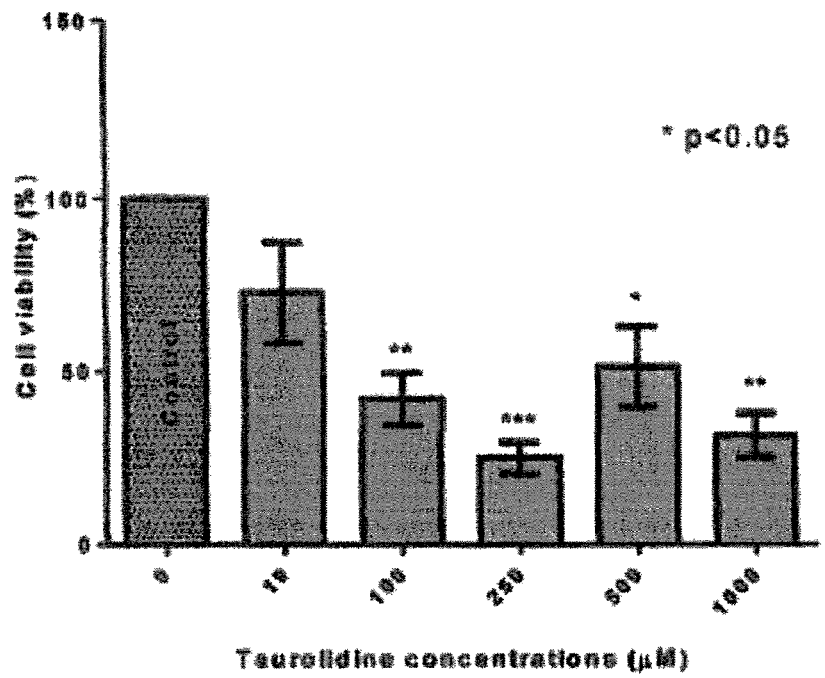
FIG. 5B graphically shows the effects of different concentrations of taurolidine on cell viability of MDA-MB-231 cell lines after 48 hours.

The results of the cell viability studies for taurolidine on cell viability of MDA-MB-231 cell lines after 24 and 48 hours are shown in FIGS. 5A and 5B.

Figure 6A:
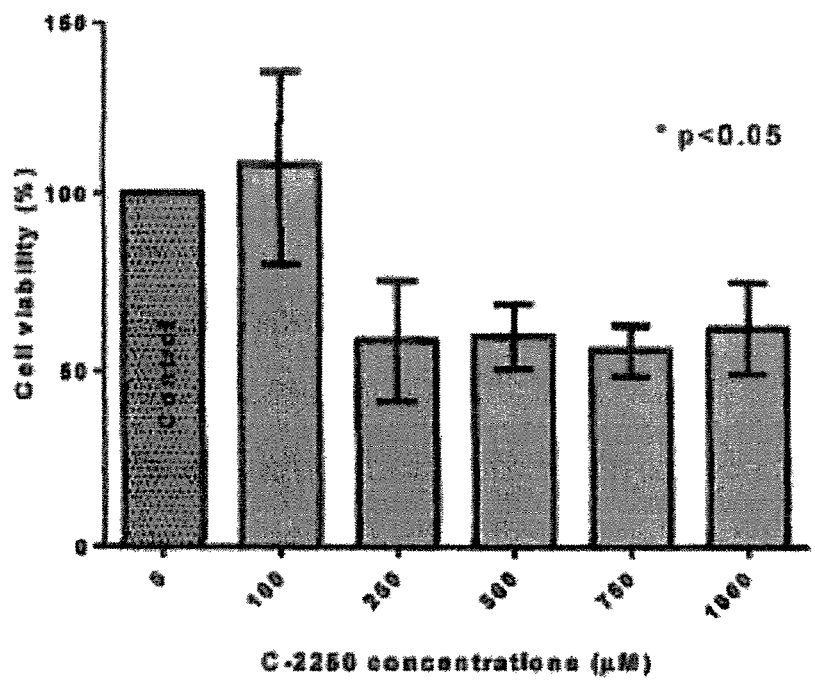
FIG. 6A graphically shows the effects of different concentrations of C-2250 on cell viability of MDA-MB-231 cell lines after 24 hours.
Figure 6B:
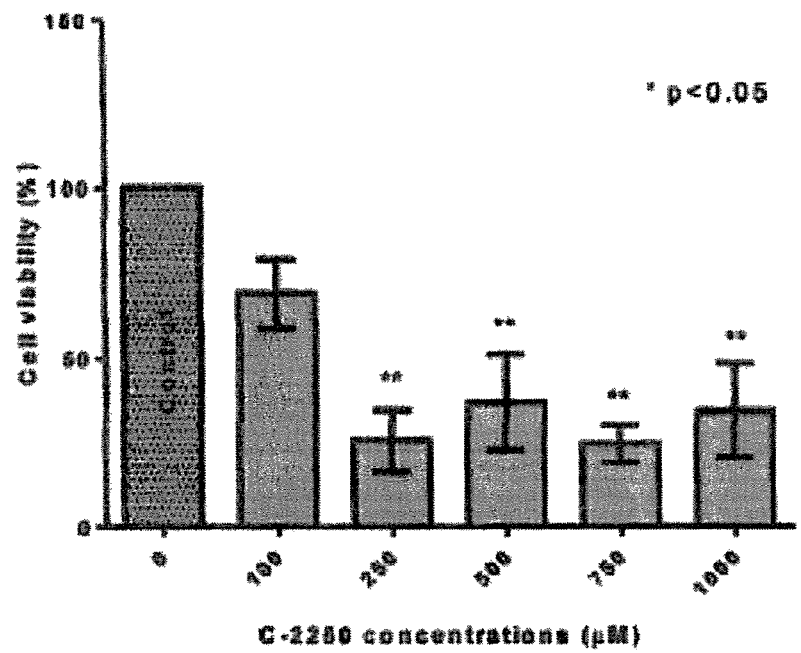
FIG. 6B graphically shows the effects of different concentrations of C-2250 on cell viability of MDA-MB-231 cell lines after 48 hours.

The results of the cell viability studies for C-2250 on cell viability of MDA-MB-231 cell lines after 24 and 48 hours are shown in FIGS. 6A and 6B.

SUMMARY

Taurolidine and C-2250 show potent antineoplastic activity in vitro, against TNBC lines. 250 µM (34 µg/ml) of C-2250 induced >50% cell death on TNBC cell lines after 48 hours. 100 µM (28 µg/ml) of taurolidine induced >50% cell death on TNBC cell lines after 48 hours.

Example 2: Human Treatment Case Study

Patient Diagnosis and History Before Study:

September of Year 1: A fifty year old Caucasian female with histological diagnosis of triple negative breast cancer of the right breast 3 cm G3, CS axilla (histologically G3 with medullary shares, ER, PR and Her 2-new negative). Disseminated lung metastasis.

Ki-67: 61% indicative of very high breast cancer cell division.

Additional evidence of ductal carcinoma in situ (DCIS) with focal vascular invasion; BRCA1 neg.

Before entering the study, the patient had been treated with numerous oncology and chemotherapy treatments including weekly neoadjuvant Taxol chemotherapy, lumpectomy with wide local excision, and adjuvant radiotherapy of the right chest wall. These treatments were ineffective and the patient developed metastatic dissemination and neutropenia, and was an end-stage (stage IV) patient.

Study Protocol:

Patient began the study having a Karnofsky score of 80%, mild neuropathy with distal emphasizes in all four extremities; and also suffered from severe pain during inspiration left lateral chest wall; for example, sneezing extremely painful, severe shortness of breath (SOS) on exertion, lack of appetite, insomnia, and exhaustion.

| Diagnosis: | Breast Cancer | ICD10: C50.9 |
|---|---|---|
| | Lung Cancer | ICD10: C78.6 |
| | Lymphadenopathy | ICD10: R59.1 |

The patient underwent a four week Treatment Protocol as follows:

1. Weekly low-dose checkpoint inhibitor therapy with PD1/PDL-1 inhibition with nivolomab (0.5 mg/kg) and CTL-4 inhibition with ipilimumab (0.3 mg/kg) over three weeks.
2. Loco-regional hyperthermia with radiofrequency fields (13.56 MHz) using Syncrotherm device 3 times per week over the thoracic region in combination with high dose vitamin C (0.5 g/kg) and alpha lipoic acid (600 mg) over three weeks followed by:
3. Long duration (6-8 hours) fever range (about 42° C.) whole body hyperthermia in combination low dose chemotherapy using cyclophosphamide 300 mg/m$^2$ to down modulate TReg cells followed by:
4. Five days high-dose IL-2 (54 Mio I.U./m$^2$ as decrescendo regime) therapy in combination with taurolidine (250 ml 2% Taurolidine, i.v.).

The inventors found that the combination of IL-2 and taurolidine was effective in inducing remission in the patient's TNBC and metastases thereof, where the other treatments had failed.

The day after completing the multidisciplinary therapy, a chest x-ray demonstrated the far advanced bilateral pulmonary metastasis. The induction of a cytotoxic T-cell response following immunotherapy may take between 1-2 months up to even 6 months. Thus, after 2 months the patient underwent a second chest x-ray which already demonstrated a 20% improvement in reduction of lung metastasis. A chest x-ray after a further 2 months demonstrated a remarkable partial remission.

Further, the patient exhibited an excellent clinical condition with a Karnofsky score of 100% and absence of shortness of breath or any other cancer-related symptoms.

Both checkpoint inhibitor types (PD 1/PDL-1 and CTL-4 inhibition) were used to avoid autoimmunity following checkpoint inhibitor therapy. Specifically, nivolomab and ipilimumab were used in an off-label use in lower dosages and metronomically in higher (weekly) sequences.

Discussion

Low-dose cyclophosphamide or gemcitabine therapy can selectively deplete T regulatory cells (Treg). Chemotherapy drugs (and irradiation) may be combined to break immune tolerance and create a tumor microenvironment for successful immune based therapies. Mild, fever range (40-42° C.) prolonged whole body hyperthermia reduces interstitial pressure in the tumor microenvironment. Additionally, hyperthermia improves immunogenicity of cancer cells and lymphocyte trafficking. High-dose IL-2 has been known to have severe side effects and, as a result, IL-2 has never gained widespread use. The main side effects of high dose IL-2 therapy are induced by vascular leak syndrome with weight gain, generalized oedema, hypotension and impaired renal function being the main features. Vascular leak syndrome (VLS) is a life-threatening toxicity induced during IL-2 treatment of cancer patients. The co-administration of taurolidine, taurultam, oxathiazin-like compounds, and combinations thereof diminishes these vascular-leak induced side effects.

In summary, the present disclosure describes the demonstrated safety and effectiveness of the combination of IL-2 and taurolidine in inducing remission in the patient's TNBC and metastases thereof, where the other treatments had failed.

Example 3: Breast Cancer Cell Line Potencies

Figure 7A:
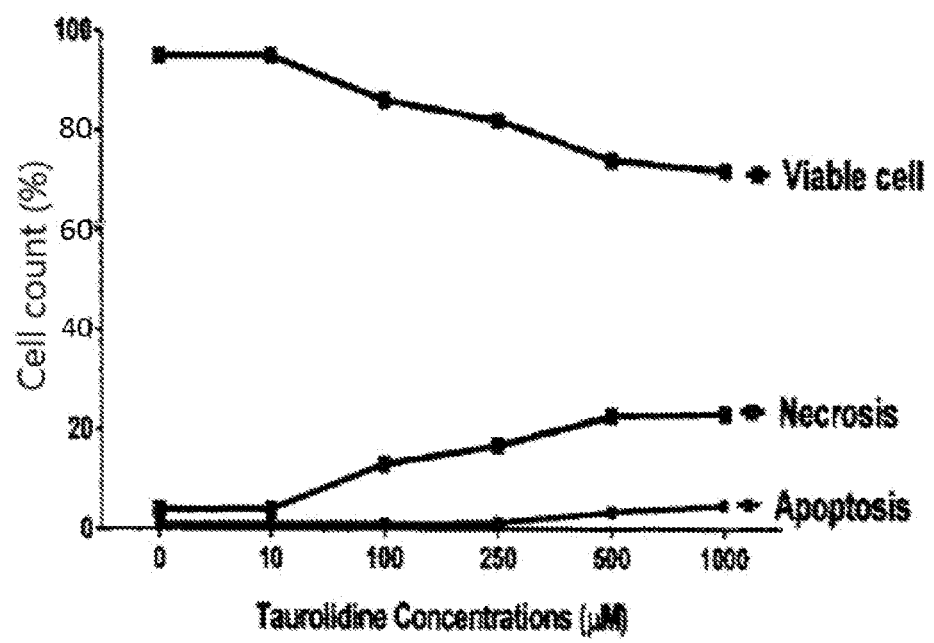
FIG. 7A graphically shows the effects of different concentrations of taurolidine on TNBC cell necrosis and apoptosis after 12 hours.
Figure 8A:
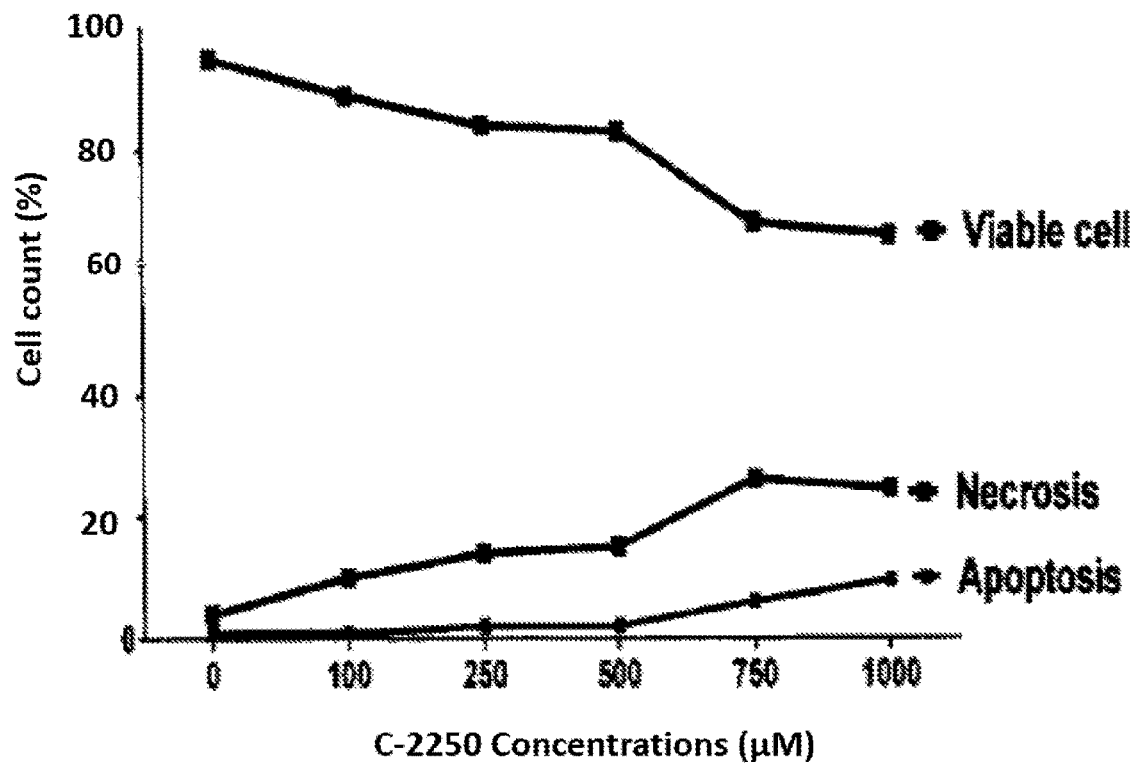
FIG. 8A graphically shows the effects of different concentrations of C-2250 on TNBC cell necrosis and apoptosis after 12 hours.

Methods: Primary and metastatic ER negative breast cancer cells (BT-20 and MDA-MB-231) and ER positive cells (BT-474 and MCF-7) were separately treated with increasing concentrations of Taurolidine and 2250 as shown in FIG. 7A and FIG. 8A. Apoptosis and necrosis were evaluated based on phosphatidylserine externalization using annexin V and propidium iodide (PI). The contribution of caspases 3, 8 and 9 on apoptosis, and autophagy was evaluated by both flow cytometry and western blotting. The impact of reactive oxygen species (ROS) was evaluated using the radical scavenger agent n-acetylcysteine (NAC) and buthionine-sulfoximine (BSO), a glutathione-depleting agent. Necroptosis was evaluated using nescrostatin-1, a potent inhibitor of the process.

Results: Dose-dependent increases in cell death were observed in ER-positive and ER-negative breast cancer cells treated separately with Taurolidine and 2250. A concentration of ≥100 μM (≥284.7 microgram) of Taurolidine and ≥250 μM (≥342 microgram) of 2250 induced >50% cell death after 48 hours (p<0.05-0.01). The cell death was most pronounced with TNBC cells. There was no evidence of autophagy involvement. Taurolidine and 2250 also induced generation of ROS, which was substantially reduced by NAC, a radical scavenger agent, and significantly increased with BSO, a glutathione-depleting agent.

Example 4: Safety of Taurolidine and C-2250

Figure 7B:
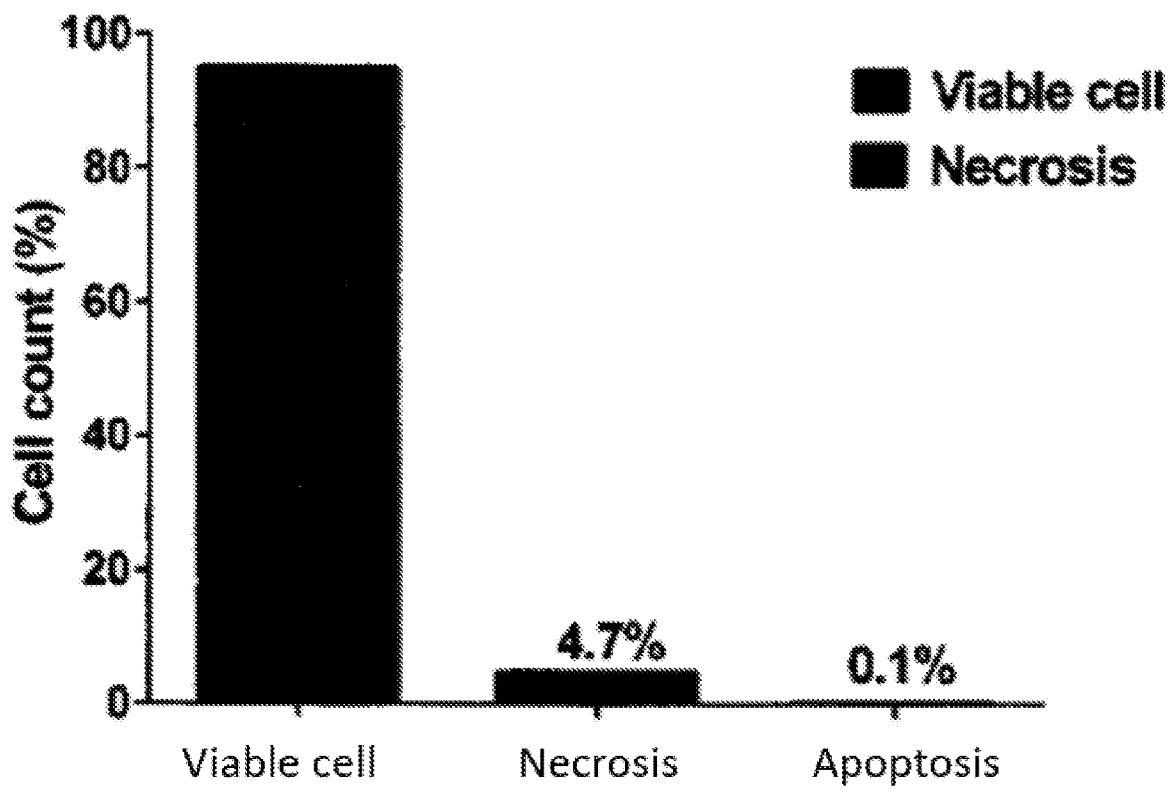
FIG. 7B graphically shows that high doses of taurolidine and C-2250 (5 mM) had no significant effect on peripherally derived human monocytes after 24 hours.

As shown in FIG. 7B, human peripheral blood monocytes were treated with Taurolidine and 2250 at concentrations of 100 microMol up to 5000 microMol and did not induce any significant cell death, demonstrating safety of Taurolidine and 2250 in non-neoplastic cells.

Example 5: Half Life of 2250

The half-life of 2250 was measured in human fresh blood at 37° C.

| Hours | Concentration of 2250 measured |
|-------|-------------------------------|
| 0-1   | 50 ppm |
| 2     | 47.7 ppm |
| 20    | 39-38.6 ppm |

The half-life was calculated to be approximately 40 hours.

As used herein, the terms about and approximately should be interpreted to include any values which are within 5% of the recited value. Furthermore, recitation of the terms 'about' and 'approximately' with respect to a range of values should be interpreted to include both the upper and lower end of the recited range. As used herein, the terms first, second, third and the like should be interpreted to uniquely identify elements and do not imply or restrict to any particular sequencing of elements or steps.

Concentrations, amounts, and other numerical data may be presented here in a range format (e.g., from about 5% to about 20%). It is to be understood that such range format is used merely for convenience and brevity, and should be interpreted flexibly to include not only the numerical values explicitly recited as the limits of the range, but also to include all the individual numerical values or sub-ranges encompassed within that range, as if each numerical value and sub-range is explicitly recited unless otherwise indicated. For example, a range of from about 5% to about 20% should be interpreted to include numerical values such as, but not limited to 5%, 5.5%, 9.7%, 10.3%, 15%, etc., and sub-ranges such as, but not limited to 5% to 10%, 10% to 15%, 8.9% to 18.9%, etc.

While the invention has been shown or described in only some of its embodiments, it should be apparent to those skilled in the art that it is not so limited, but is susceptible to various changes without departing from the spirit and scope of the invention. Furthermore, it is to be understood that the form of the invention shown and described is to be taken as presently preferred embodiments. Various modifications and changes may be made to each and every processing step as would be obvious to a person skilled in the art having the benefit of this disclosure. It is intended that the following claims be interpreted to embrace all such modifications and changes and, accordingly, the specification is to be regarded in an illustrative rather than a restrictive sense. The disclosure, including any readily discernible variants of the teachings herein, defines, in part, the scope of the foregoing claim terminology such that no inventive subject matter is dedicated to the public. Moreover, it is intended that the appended claims be construed to include alternative embodiments.

The invention claimed is:

1. A method of treating a patient suffering from triple negative breast cancer (TNBC) comprising treating the patient with C-2250

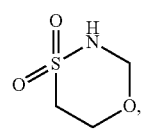

wherein C-2250 is administered intravenously, orally or a combination thereof.

2. The method of claim 1, wherein the patient is treated with C-2250 administered intravenously, orally or a combination thereof during a preoperative and/or intraoperative period and administered oral taurolidine, taurultam, one or more compound selected from

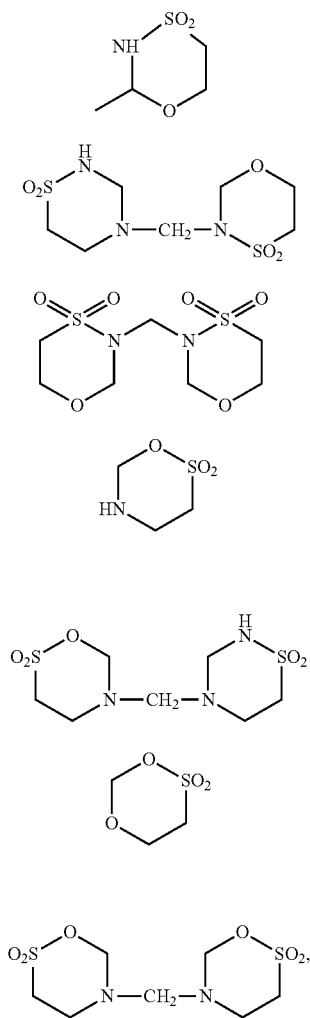

or a combination thereof postoperatively.

3. The method of claim 1, wherein the patient is treated with C-2250 administered intravenously, orally or a combination thereof during a preoperative and/or intraoperative period and administered oral C-2250 postoperatively.

4. The method of claim 1, comprising treating the patient with a plurality of treatments comprising administering C-2250 and Interleukin-2 (IL-2) to the patient in an effective amount without inducing toxic side effects associated with IL-2 monotherapy.

5. The method of claim 4, wherein IL-2 is administered at a dose between 25 and 60 Mio I.U./m².

6. The method of claim 4, wherein IL-2 and C-2250 are co-administered with one or more of the following compounds:

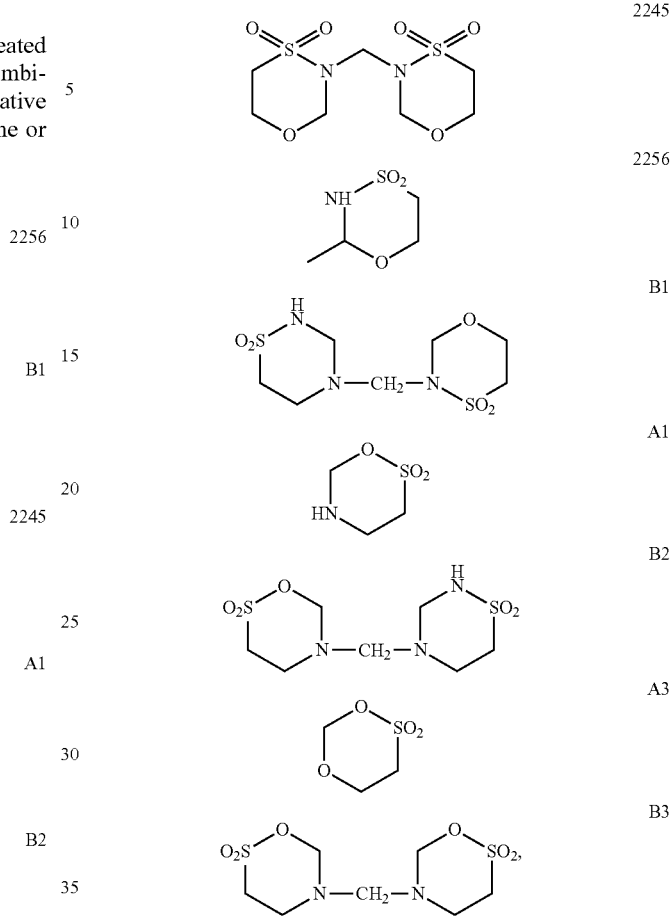

taurolidine and taurultam.

7. The method of claim 1, wherein the patient is administered loco-regional hyperthermia treatment, whole body hyperthermia (WBHT) or a sequential combination of loco-regional and whole body hyperthermia treatment.

8. The method of claim 1, wherein the patient is administered one, two or three checkpoint inhibitors.

9. The method of claim 8, wherein the checkpoint inhibitors are administered at dosage amounts below Food and Drug Administration (FDA) approved dosage amounts for the one or more checkpoint inhibitors.

10. The method of claim 8, wherein the checkpoint inhibitors are not human programmed death receptor-1 (PD-1) blocking antibodies and/or human cytotoxic T-lymphocyte antigen 4 (CTLA-4)-blocking antibodies.

11. The method of claim 8, wherein the checkpoint inhibitors are administered at doses of 0.1-1.8 mg/kg weekly, every two weeks, or every three weeks.

12. The method of claim 1, wherein the patient is administered low dose chemotherapy.

13. The method of claim 12, wherein the patient is administered cyclophosphamide, gemcitabine, 5-fluorouracil, paclitaxel, cisplatin, and carboplatin.

14. The method of claim 12, wherein the low dose chemotherapy comprises administering an anti-tumor agent effective for down-modulating TReg cells in an amount effective for down-modulating, but below a cytotoxic level.

15. The method of claim 1, comprising administering PD-1 and CTLA-4 checkpoint inhibitors to the patient and concurrently treating the patient with hyperthermia treatment.

16. The method of claim 15, wherein the hyperthermia treatment is administered to the patient for 3-5 weeks.

17. The method of claim 1, wherein the patient is treated with C-2250 and an anti-cancer drug.

18. The method of claim 17, wherein the anti-cancer drug is one or more of IL-2, cyclophosphamide, gemcitabine, 5-fluorouracil, paclitaxel, cisplatin, and carboplatin.

19. The method of claim 17, comprising administering one or more of the following compounds:

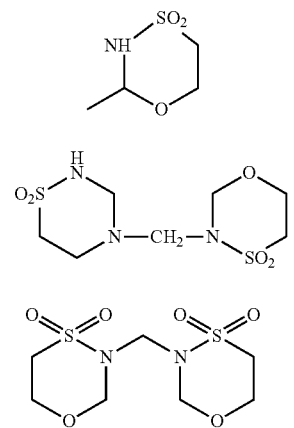

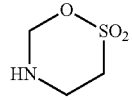

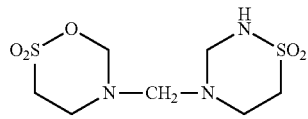

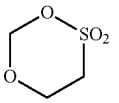

taurolidine and taurultam.

20. The method of claim 1, further comprising treating the patient with a plurality of treatments selected from the group consisting of a checkpoint inhibitor, hyperthermia, low dose chemotherapy, and Interleukin-2 (IL-2).

21. The method of claim 17, further comprising treating the patient with anastrozole, letrozole, tamoxifen, or a combination thereof.

* * * * *